US00PP17983P2

(12) United States Plant Patent
Cabrera Avalos

(10) Patent No.: US PP17,983 P2
(45) Date of Patent: Sep. 4, 2007

(54) BLACKBERRY PLANT NAMED 'DRISCOLL THORNLESS SLEEPING BEAUTY'

(50) Latin Name: ***Rubus* L.**
Varietal Denomination: Driscoll Thornless Sleeping Beauty

(75) Inventor: Reynaldo Cabrera Avalos, Jacona (MX)

(73) Assignee: Driscoll Strawberry Associates, Inc., Watsonville, CA (US)

( * ) Notice: Subject to any disclaimer, the term of this patent is extended or adjusted under 35 U.S.C. 154(b) by 233 days.

(21) Appl. No.: 10/969,663

(22) Filed: Oct. 20, 2004

(51) Int. Cl.
*A01H 5/00* (2006.01)

(52) U.S. Cl. ..... Plt./203

(58) Field of Classification Search ..... Plt./203
See application file for complete search history.

*Primary Examiner*—Kent Bell
*Assistant Examiner*—Annette H Para
(74) *Attorney, Agent, or Firm*—Jones Day

(57) ABSTRACT

The present invention relates to a new and distinct cultivar of blackberry plant named 'Driscoll Thornless Sleeping Beauty.' The new cultivar is distinguished from other blackberry cultivars by its early season crop, large fruit size and thornless canes. 'Driscoll Thornless Sleeping Beauty' produces fruit with improved quality and shipping characteristics. The new cultivar is distinguished from its parent by having thornless canes.

3 Drawing Sheets

1. Latin name of the genus and species of the plant claimed: The variety is botanically identified as *Rubus* L. subgenus *Rubus*.

1.2 Variety denomination: The Blackberry variety denomination is 'Driscoll Thornless Sleeping Beauty'.

2. BACKGROUND OF THE INVENTION

This invention relates to a new cultivar of blackberry called 'Driscoll Thornless Sleeping Beauty'. The new cultivar was developed from a spineless mutant of the patented cultivar 'Sleeping Beauty' (U.S. Plant Pat. No. 13,758 P3). 'Sleeping Beauty' was developed from a hybridization of the female cultivar 'Brazos' (unpatented) with the male cultivar 'Hull Thornless' (unpatented). The new variety was discovered in 2001 in a field of 'Sleeping Beauty' near Jacona, Mexico where after it was propagated to produce plants for planting trials in 2002. The new cultivar was selected in 2001 for its thornless canes. The cultivar has been asexually propagated in Mexico by hardwood cuttings and reproduced true to type plants.

3. SUMMARY OF THE INVENTION

The present invention provides a new and distinct blackberry cultivar named 'Driscoll Thornless Sleeping Beauty'. The variety is a complex *Rubus* hybrid, which can be characterized as an upright tetraploid with considerable *R. allegheniensis* background with other species such as *R. trivialis, R. argutus* and *R. ulmifolious* also appearing in its background. The new cultivar produces a floricane crop which begins in mid May and continues until mid-August. The new blackberry variety is distinguished from other varieties by a number of characteristics as set forth in Table 1. In particular, the new cultivar is distinguished by its early season of fruit ripening, its large fruit size, low-chill requirement, and thornless canes.

4. COMPARISON TO SIMILAR VARIETIES

The variety most similar to 'Driscoll Thornless Sleeping Beauty' from those known to us is 'Sleeping Beauty'. 'Driscoll Thornless Sleeping Beauty' is particularly different from 'Sleeping Beauty' by having thornless canes. Further detailed comparison of 'Driscoll Thornless Sleeping Beauty' to 'Sleeping Beauty' is presented in Table 1.

5. BRIEF DESCRIPTION OF THE DRAWINGS

The accompanying photographs show typical specimens of the fruit, leaves and shoot of the new cultivar, in color as nearly true as reasonably possible in color illustrations of this type.

Figure 1:
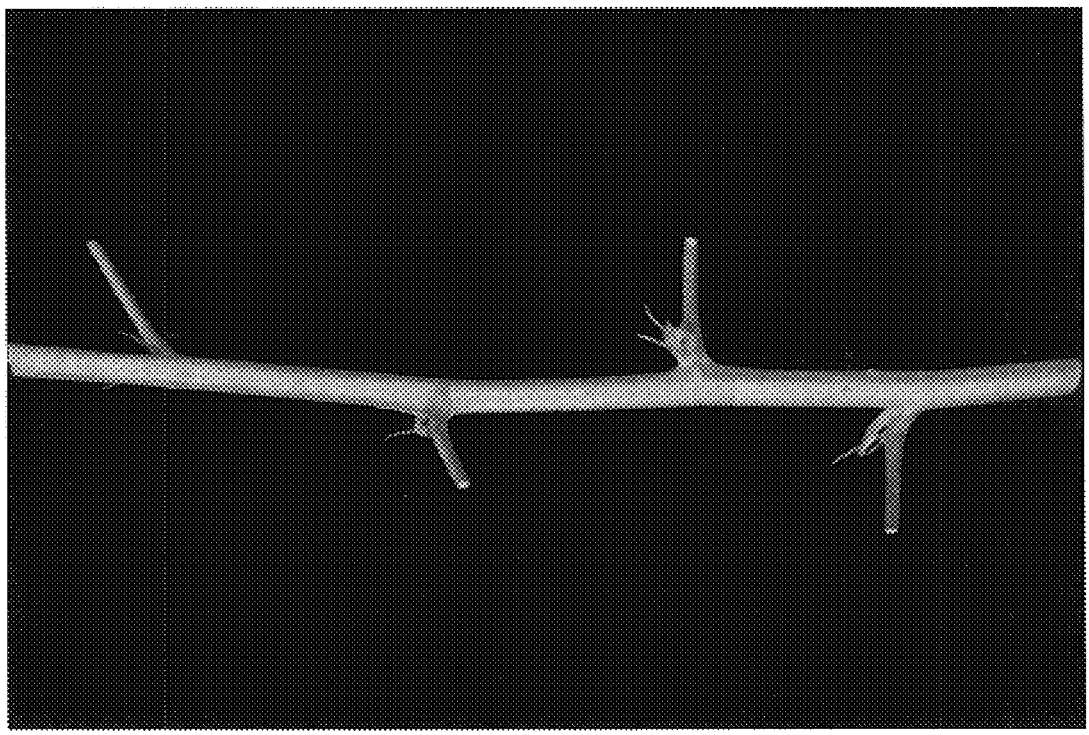

FIG. 1. is a photograph showing a close-up view of a primocane shoot.

Figure 2:
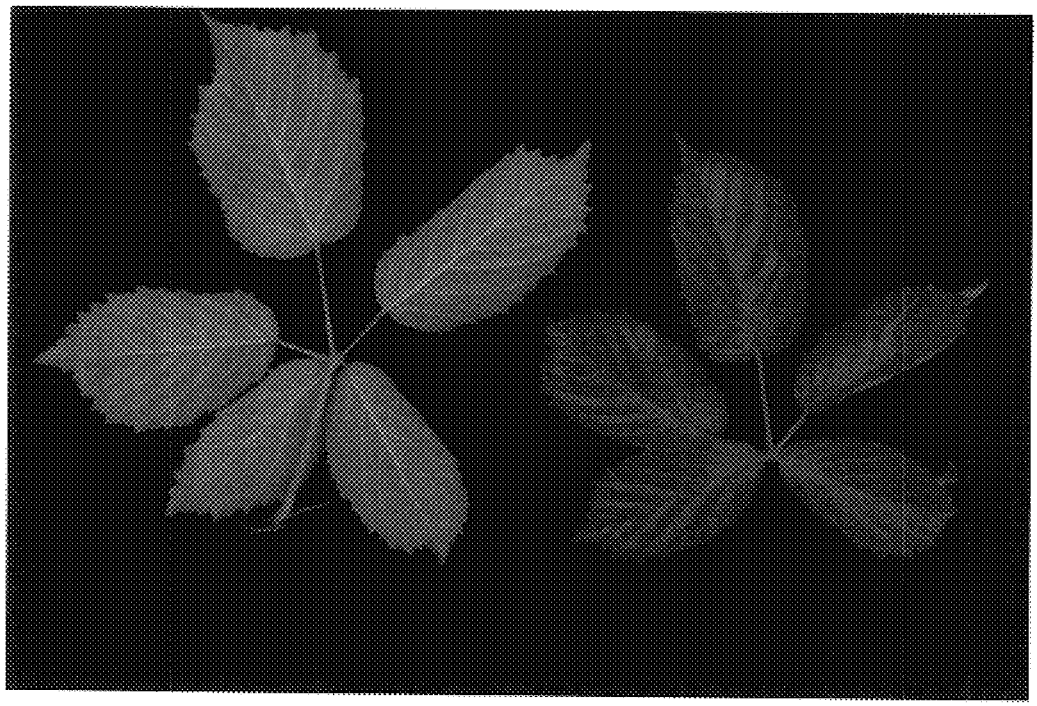

FIG. 2. is a photograph showing the upperside and underside of two mature leaves of 'Driscoll Thornless Sleeping Beauty'.

Figure 3:
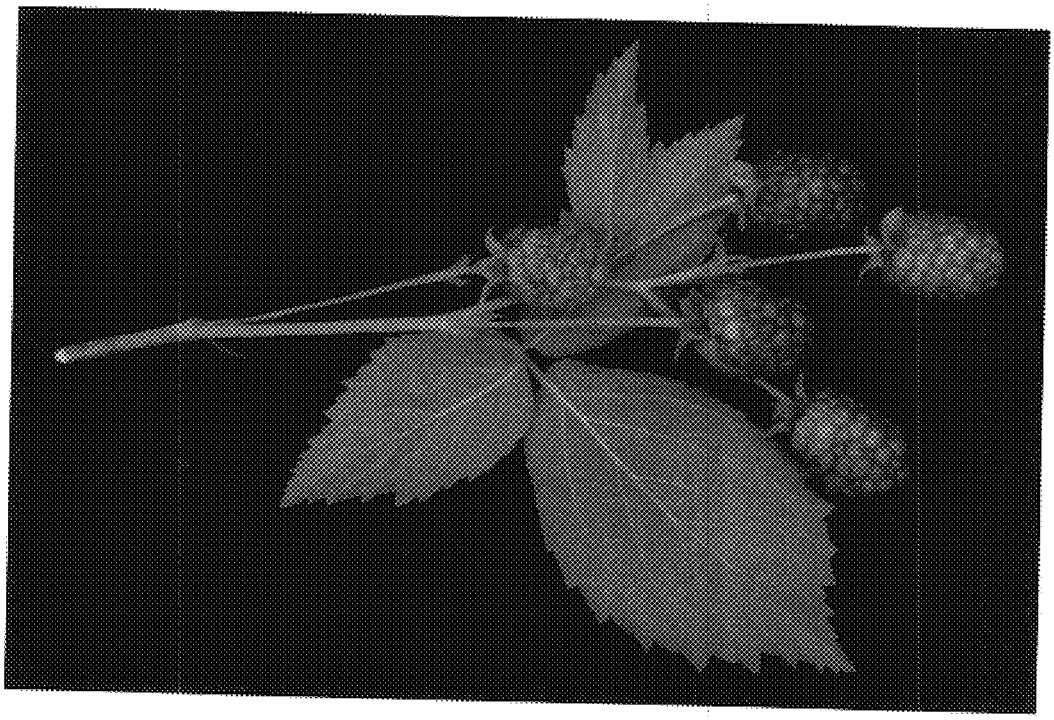

FIG. 3. is a photograph of a 'Driscoll Thornless Sleeping Beauty' fruiting lateral with fruit in various stages of development.

6. DESCRIPTION OF THE NEW VARIETY

The following detailed description of the new blackberry cultivar, 'Driscoll Thornless Sleeping Beauty', is based upon recorded observations of plants and fruit grown between 2002 and 2004 in Zamora, Mexico and is believed to apply to plants of the 'Driscoll Thornless Sleeping Beauty' cultivar grown in similar conditions of soil and climate elsewhere. Plants were planted on soil previously pre-plant fumigated and regularly fertilized and irrigated with drip irrigation. This description is in accordance with terminology used by the International Union for the Protection of New Varieties of Plants (UPOV). Throughout this specification, color names beginning with a small letter signify that the name of the color, as used in common speech, is aptly descriptive. Color data beginning with a capital letter and followed by an alphanumeric code indicate the most similar color designations as provided by The Royal Horticultural Society (R.H.S.) Colour Chart published by The Royal Horticultural Society of London, England. Color designations, color descriptions, and other phenotypical descriptions may deviate from the stated values and descriptions depending upon variation in environmental, seasonal, climatic and cultural conditions.

6.1 CHARACTERISTICS OF THE NEW VARIETY

Table 1 provides information on the plant and fruit characteristics of the new blackberry cultivar 'Driscoll Thornless Sleeping Beauty' compared with characteristics of the patented cultivar 'Sleeping Beauty'. 'Sleeping Beauty' is an important cultivar for fresh market shipping, and thus comparable to the proposed use of the new variety, 'Driscoll Thornless Sleeping Beauty'. Observations of 'Driscoll Thornless Sleeping Beauty' and 'Sleeping Beauty' were taken in side-by-side comparison in 2004 in Zamora, Mexico.

Fruit of the new cultivar is particularly characterized and distinguished from 'Sleeping Beauty' by thornless canes.

The bud burst of 'Driscoll Thornless Sleeping Beauty' is early, with bud burst, generally, in late January. Additionally, 'Driscoll Thornless Sleeping Beauty' flowers early, with flowering, generally, beginning in late March. 'Driscoll Thornless Sleeping Beauty' is moderately productive and produces most of its crop in the early part of the harvest season. Canes of 'Driscoll Thornless Sleeping Beauty' are vigorous, and have buds with a low to moderate winter chill requirement.

TABLE 1

PLANT CHARACTERISTICS OF 'DRISCOLL THORNLESS SLEEPING BEAUTY', 'BRAZOS', AND 'SLEEPING BEAUTY'

| | 'Driscoll Thornless Sleeping Beauty' | 'Brazos' | 'Sleeping Beauty' |
|---|---|---|---|
| GENERAL | | | |
| Vigor | High | High | High |
| Growth habit | Upright | Semi-Upright | Upright |
| Productivity | Moderate | High | Moderate |
| Self-fruitfulness | Self-fruitful | Self-fruitful | Self-fruitful |
| Time of bud burst | Early | Early | Early |
| CANES | | | |
| Primocanes | | | |
| Young shoot pigmentation | 144A yellow green | 144A yellow green | 144A yellow green |
| Glucosity (waxy) bloom) | Weak | Absent or weak | Weak |
| Cane cross section (from mid cane of primocane) | Angular | Grooved | Angular to grooved |
| Dormant cane color | Brown to purple brown | | Brown to purple brown |
| Spines | Absent | Present | Present |
| Pubescence on canes | Present | Present | Absent |
| LEAVES | | | |
| Relief between veins | Medium | Medium | Medium |
| Number of leaflets | Usually 3 | Usually 3 | Usually 3 |
| Glossiness | Medium | Medium | Medium |

TABLE 1-continued

PLANT CHARACTERISTICS OF 'DRISCOLL THORNLESS SLEEPING BEAUTY', 'BRAZOS', AND 'SLEEPING BEAUTY'

| | 'Driscoll Thornless Sleeping Beauty' | 'Brazos' | 'Sleeping Beauty' |
|---|---|---|---|
| Cross section | Flat | Concave | Flat |
| Terminal leaflet | | | |
| Length (cm) | 6.1 | 7.4 | 6.4 |
| Width (cm) | 4.3 | 5.1 | 4.0 |
| Shape | Ovate | Ovate | Ovate |
| Tip | Acute | Acute | Acute |
| Base | Rounded to cordate | Rounded | Rounded to cordate |
| Margin | Doubly serrated | Double serrated | Doubly serrated |
| Lateral leaflet | | | |
| Length (cm) | 4.8 | 6.0 | 5.4 |
| Width (cm) | 3.2 | 3.9 | 3.4 |
| Overlap of lateral Leaflets | No | No | No |
| Shape | Elliptical | Elliptical | Elliptical |
| Tip | Acute | Acute | Acute |
| Base | Rounded | Rounded | Rounded |
| Margin | Doubly serrate | Doubly serrate | Doubly serrate |
| Rachis length (between terminal leaflet and adjacent lateral (leaflets) (cm) | 1.2 | 1.5 | 1.4 |
| Petiole | | | |
| Length (cm) | 3.5 | 5.0 | 3.8 |
| Pigmentation of upper surface | 146A yellow green | 144A yellow green | 146A yellow green |
| Pigmentation of Underside | 144A yellow green | 144B yellow green | 144A yellow green |
| Stipule orientaion | Clasping | Clasping | Clasping |
| Color | | | |
| Face | 147A yellow green | 147A yellow green | 147A yellow green |
| Underside | 146A yellow green | 146A yellow green | 146A yellow green |
| FLOWERS | | | |
| Flowering period time of beginning of flowering | Early | Early | Early |
| Flower size | Medium | Large | Medium |
| Flower diameters (cm) | 3.9 | 6.0 | 4.4 |
| Flower number (at 3rd node from tip of lateral mean and range) | 4.0 | 3.8 | 4.0 |
| Petal | | | |
| Length (cm) | 2.0 | 2.7 | 2.3 |
| Width (cm) | 1.3 | 2.2 | 1.6 |
| Color | 155D white | 155D white | 155D white |
| Sepal color | 144A yellow green | 144A yellow green | 144A yellow green |
| Pedicel | | | |
| Coloration | absent | absent | absent |
| Length | Medium | Medium-short | Medium |
| FRUIT | | | |
| Fruit harvest season | Early | Early | Early |
| Color | Black | Black | Black |
| Immature | 187A greyed-purple | 187A greyed-purple | 187A greyed-purple |
| Maturing | 202A black | 202A black | 202A black |

TABLE 1-continued

PLANT CHARACTERISTICS OF 'DRISCOLL THORNLESS SLEEPING BEAUTY', 'BRAZOS', AND 'SLEEPING BEAUTY'

| | 'Driscoll Thornless Sleeping Beauty' | 'Brazos' | 'Sleeping Beauty' |
|---|---|---|---|
| Mature fruit | 202A black | 202A black | 202A black |
| Glossiness | Medium | Medium | Medium |
| Shape | Elliptic | Ovate | Elliptic |
| Dimensions | | | |
| Fruit size | Medium | Large | Medium |
| Length (cm) | 2.7 | 3.1 | 2.5 |
| Width (cm) | 2.0 | 2.4 | 2.1 |
| Soluble solids (%) | 13.5 | 9.0 | 12.3 |
| Titratable acidity (% as citric acid) | 2.9 mL NaOH | 2.3 mL NaOH | 3.2 mL NaOH |
| Number of druplets/fruit | 80 | 79 | 77 |

TABLE 1-continued

PLANT CHARACTERISTICS OF 'DRISCOLL THORNLESS SLEEPING BEAUTY', 'BRAZOS', AND 'SLEEPING BEAUTY'

| | 'Driscoll Thornless Sleeping Beauty' | 'Brazos' | 'Sleeping Beauty' |
|---|---|---|---|
| Firmness | Medium | Medium | Medium |
| Seeds | | | |
| Weight (mg) | 4.3 | 3.6 | 4.2 |
| Color | 152B yellow green | 152D yellow green | 152B yellow green |

What is claimed:

1. A new and distinctive cultivar of blackberry plant, substantially as shown and described.

* * * * *